(12) United States Patent
Foerderer

(10) Patent No.: US 7,313,993 B2
(45) Date of Patent: Jan. 1, 2008

(54) FEEDING MECHANISM FOR A MICROTOME

(75) Inventor: Klaus Foerderer, Rauenberg (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 109 days.

(21) Appl. No.: 10/382,287

(22) Filed: Mar. 5, 2003

(65) Prior Publication Data

US 2003/0167892 A1 Sep. 11, 2003

(30) Foreign Application Priority Data

Mar. 9, 2002 (DE) .................... 102 10 408

(51) Int. Cl.
*B23D 25/00* (2006.01)
(52) U.S. Cl. .................. 83/437.6; 83/915.5; 83/721
(58) Field of Classification Search ................ 83/602, 83/613, 915.5, 628, 697, 167, 401, 707, 435.25, 83/437.1, 437.6, 932, 435.19, 435.11, 703, 83/777, 721; 74/18.2, 22 A, 27, 567, 570; 269/66
See application file for complete search history.

(56) References Cited

U.S. PATENT DOCUMENTS

| | | | | |
|---|---|---|---|---|
| 1,217,521 A * | 2/1917 | Snyder | ................... | 227/153 |
| 1,764,300 A * | 6/1930 | Hamman | ................... | 470/19 |
| 2,458,160 A * | 1/1949 | Grappe | ................... | 83/549 |
| 2,704,576 A * | 3/1955 | Rosauer | ................... | 83/221 |
| 2,768,560 A * | 10/1956 | Hirson | ................... | 493/364 |
| 3,132,608 A * | 5/1964 | Leuze | ................... | 425/311 |
| 3,203,290 A * | 8/1965 | Ashby | ................... | 83/171 |
| 3,768,359 A * | 10/1973 | Koefferlein | ................... | 234/115 |
| 3,828,641 A * | 8/1974 | Sitte | ................... | 83/703 |
| 4,495,844 A * | 1/1985 | Jackson et al. | ................... | 83/715 |
| 4,502,358 A * | 3/1985 | Behme | ................... | 83/699.61 |
| 4,505,175 A * | 3/1985 | Reichel | ................... | 83/703 |
| 5,461,957 A * | 10/1995 | Koch et al. | ................... | 83/713 |
| 5,522,294 A * | 6/1996 | Krumdieck | ................... | 83/411.1 |
| 5,628,502 A * | 5/1997 | Amarakoon | ................... | 270/58.07 |
| 5,740,717 A * | 4/1998 | Sowden et al. | ................... | 83/879 |
| 5,906,148 A * | 5/1999 | Aihara et al. | ................... | 83/72 |
| 6,374,715 B1 * | 4/2002 | Takatsuka | ................... | 83/620 |

FOREIGN PATENT DOCUMENTS

| | | |
|---|---|---|
| DE | 3615714 A1 | 11/1987 |
| DE | 3727975 A1 | 3/1989 |

\* cited by examiner

*Primary Examiner*—Kenneth E. Peterson
*Assistant Examiner*—Phong Nguyen
(74) *Attorney, Agent, or Firm*—Hodgson Russ LLP

(57) ABSTRACT

A feed device (1) for a microtome, in particular for a cryostat microtome, for setting the cut thickness of the specimen (2) to be sectioned, is described. In order to set the cut thickness, either the cutting knife or the specimen holder (3) is mounted on a slide (8) in a slide guide (4) and is connected non-positively to a drive motor (5). The drive motor (5) is connected either to an eccentric cam (6) or to a helical cam (7), and the nonpositive connection between the motor (5) and the slide is accomplished via the eccentric cam (6) or the helical cam (7).

7 Claims, 1 Drawing Sheet

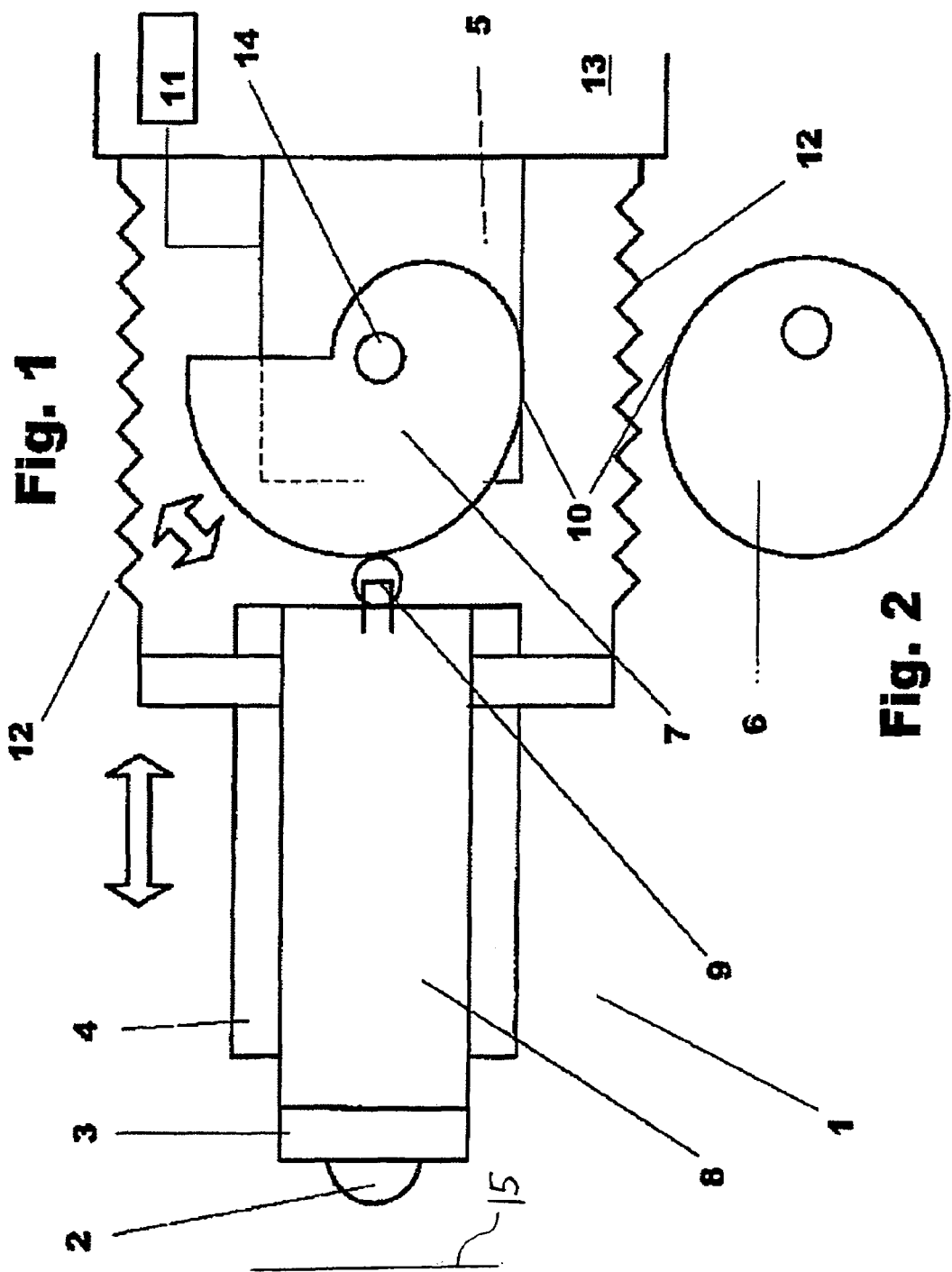

FEEDING MECHANISM FOR A MICROTOME

CROSS REFERENCE TO RELATED APPLICATIONS

This application claims priority of the German patent application 102 10 408.5 which is incorporated by reference herein.

FIELD OF THE INVENTION

The invention concerns an advance mechanism for a microtome, in particular for a cryostat microtome, for providing cut thickness displacement between a knife of the microtome and a specimen to be cut.

BACKGROUND OF THE INVENTION

Microtomes are designed for precise and thin cutting of preparations for subsequent microscopic examination. For that purpose, a relative motion takes place between the cutting knife and the preparation. Once a cut has been made, the preparation and the knife must be advanced again with respect to one another by an amount equal to the desired cut thickness. This is generally accomplished with a spindle drive system and a movable nut. Rotation of the spindle causes the nut to move, and the desired advance motion takes place between the knife and the preparation or the specimen holder carrying the preparation.

A spindle drive system of this kind is depicted and described in DE 37 27 975 A1. This spindle drive system is characterized in that the usual play between the nut and spindle is minimized by way of a nut, in two parts braced against one another, that runs on the spindle. Largely zero-clearance advance, and thus precise cutting of the specimens, is thus possible.

These drive systems have proven successful for microtomes under normal conditions, but are insufficiently usable in cryostat microtomes. Because of the large temperature differences (from ambient temperature to −60° C.) during operation of a cryostat microtome, and the differing temperature coefficients of the materials used, a clearance that is in fact undesirable must be permitted in the connection between spindle and nut. Otherwise the risk exists that the drive system will jam.

A device that solves this problem is known from DE 36 15 714 A1. This document describes a motorized advance drive system for a specimen head of a cryostat microtome in which the specimen head is mounted slidingly via a sleeve, and is connected nonpositively to a motorized micrometer. As a result of the nonpositive connection, the preparation arm can be both advanced onto the cutting knife and removed again. With this apparatus, however, provision is also made to encapsulate the entire motorized micrometer drive system in a separate housing, and to heat that housing. Encapsulating and heating a microtome in a cryostat of course requires a great deal of complexity. In addition, a constant temperature setting for the cold portion of the cryostat is not possible with a design of this kind.

SUMMARY OF THE INVENTION

It is therefore the object of the present invention to develop the feed mechanism for a microtome in such a way that heating of the drive system can be omitted, but a zero-clearance and precise movement between the specimen and the knife is nevertheless possible for adjustment of the cut thickness.

This object is achieved according to the present invention by the features disclosed and claimed herein.

The invention is characterized in that in order to set the cut thickness of the specimen to be sectioned, the usual spindle drive system has been replaced by a guided slide element and a motorized drive system non-positively connected via an eccentric cam or a helical cam. As a result, temperature-sensitive positive connections for the linear drive system are no longer present. Precision in the advance system is now dependent only on the motor, preferably a stepper motor, and the helical cam or eccentric cam connected thereto. Undesired jamming of the drive system is reliably prevented.

In a further embodiment of the invention, provision is made for the specimen holder to be joined to the slide, and for the latter to be guided slidingly in a slide guide.

In a further embodiment of the invention, the slide is equipped, opposite the specimen holder, with a track roller or a slide element. The track roller or slide element serves as contact point for the outer periphery of the eccentric cam or the outer periphery of the helical cam.

In a further embodiment of the invention, the drive device is equipped with a stepper motor that, in order to advance a predetermined amount, is connected to a control device. The result of this is that even non-linearly proportional advance movements when advancing by way of the eccentric cam can be converted into linearly proportional movements. The necessary pulses for the stepper motor are calculated on the basis of the position of the eccentric cam or of the stepper motor.

BRIEF DESCRIPTION OF THE DRAWINGS

The invention is presented and explained in more detail in an exemplary embodiment with reference to the drawings, in which:

FIG. 1 is a schematic sketch of a feed device with a helical cam in accordance with an embodiment of the present invention; and FIG. 2 shows an eccentric cam as replacement for the helical cam shown in FIG. 1.

DETAILED DESCRIPTION OF THE INVENTION

FIG. 1 shows a feed device 1 for a microtome having a specimen 2 to be sectioned, which is arranged on a specimen holder 3. Specimen holder 3 is mounted on a slide 8 linearly moveable in a slide guide 4, and is configured to be moveable in the double-arrow direction. Arranged on slide 8 at an end opposite specimen 2 is a track roller 9 that runs on outer periphery 10 of a helical cam 7 (see FIG. 1) and is non-positively joined to helical cam 7. For that purpose, a tension spring 12 is arranged between slide 8 and a stationary part 13 of the microtome.

Helical cam 7 is arranged on a drive shaft 14 of a drive motor 5, which preferably is embodied as a stepper motor and is connected to a control device 11.

Helical cam 7 is rotated stepwise by motor 5. Track roller 9 thereby rolls on the outer periphery of helical cam 7, and slide 8 is moved linearly in slide guide 4. The non-positive connection between helical cam 7 and track roller 9 is maintained by way of tension spring 12.

FIG. 2 shows an eccentric cam 6 that can be used instead of helical cam 7 of FIG. 1. The use of an eccentric cam 6 has the advantage, as compared to a helical cam 7, that a wider usable adjustment range for slide 8 can be provided. A disadvantage, however, is that rotating the eccentric cam by identical amounts does not result in identical linear displacements of slide 8. This must be compensated for by way of control device 11 and stepper motor 5. Helical cam 7, on the other hand, can be configured in such a way that identical rotations result in identical linear displacements.

| PARTS LIST | |
|---|---|
| 1 | Feed device |
| 2 | Specimen |
| 3 | Specimen holder |
| 4 | Slide guide |
| 5 | Drive motor |
| 6 | Eccentric cam |
| 7 | Helical cam |
| 8 | Slide |
| 9 | Track roller |
| 10 | Outer periphery of 6 or 7 |
| 11 | Control device |
| 12 | Tension spring |
| 13 | Stationary part |
| 14 | Drive shaft of 5 |
| 15 | Microtome knife |

What is claimed is:

1. A cryostat microtome comprising:
   a stationary microtome part;
   a microtome knife;
   a slide guide defining a linear travel path toward and away from said microtome knife to adjust thickness of cut;
   a slide element guided by said slide guide for movement relative to said slide guide along said linear travel path;
   a specimen holder mounted on said slide element for holding a specimen to be cut by said microtome knife;
   a drive motor;
   a cam driven by said drive motor and engaged by said slide element, wherein said slide element includes a roller arranged to engage an outer periphery of said cam; and
   at least one spring having a first end connected to said stationary microtome part and a second end connected to said slide element, said at least one spring acting to bias said slide element toward engagement with said cam to maintain a non-positive connection between said slide element and said cam;
   wherein said cam is located between said slide element and a location where said at least one spring is connected to said stationary microtome part.

2. The cryostat microtome according to claim 1, wherein said cam is a helical cam.

3. The cryostat microtome according to claim 1, wherein said cam is an eccentric cam.

4. The cryostat microtome according to claim 1, wherein said roller defines a roller track for receiving said outer periphery of said cam.

5. The cryostat microtome according to claim 1, wherein the drive motor is a stepper motor.

6. The cryostat microtome according to claim 5, further comprising a control unit connected to said stepper motor, whereby a predetermined relative displacement between said specimen and said knife can be set.

7. The cryostat microtome according to claim 1, wherein said at least one spring is a tension spring.

* * * * *